United States Patent [19]

Kempe

[11] Patent Number: 4,653,473

[45] Date of Patent: Mar. 31, 1987

[54] METHOD AND ARTICLE FOR PAIN REDUCTION USING RADIATION-SHIELDING TEXTILE

[76] Inventor: Frieder K. Kempe, P.O. Box 278, Coquitlam, British Columbia, Canada, V3C 4K6

[21] Appl. No.: 602,592

[22] Filed: Apr. 20, 1984

[51] Int. Cl.⁴ .............................................. A61N 1/16
[52] U.S. Cl. ................................ 128/1 R; 139/425 R; 361/220
[58] Field of Search ................... 128/1 R, 82.1, 132 R, 128/165, 362, 379–382, 484, 419 R; 2/1, 16, 22, 69, 69.5, DIG. 7; 361/220, 223, 224; 174/55 B; 139/425 R

[56] References Cited

U.S. PATENT DOCUMENTS

| | | | |
|---|---|---|---|
| 100,591 | 3/1870 | Bracher | 139/425 R |
| 1,965,542 | 7/1934 | Colvin | 57/230 |
| 2,348,771 | 9/1945 | Ryan | 139/425 R |
| 2,408,368 | 10/1946 | Brickman | 139/425 R |
| 3,047,860 | 7/1962 | Swallow et al. | 343/18 B |
| 3,288,175 | 11/1966 | Valko | 139/425 R |
| 3,699,590 | 10/1972 | Webber et al. | 361/220 X |
| 3,828,543 | 8/1974 | Goodbar et al. | 139/425 X |
| 4,211,261 | 7/1980 | Mehta | 139/425 R |
| 4,398,277 | 8/1983 | Christiansen et al. | 361/220 |

FOREIGN PATENT DOCUMENTS

| | | | |
|---|---|---|---|
| WO82/02148 | 7/1982 | PCT Int'l Appl. | 128/1 R |
| 777771 | 6/1957 | United Kingdom | 128/1 R |
| 2025237 | 1/1980 | United Kingdom | 128/132 R |

Primary Examiner—Lee S. Cohen
Attorney, Agent, or Firm—Chernoff, Vilhauer, McClung & Stenzel

[57] ABSTRACT

A method of reducing pain resulting from exposed or damaged nerve ends, such as the pain in amputees commonly referred to as phantom limb pain is disclosed. The method may also reduce pain resulting from arthritis. This method involves covering the affected area with a radiation-shielding textile, whether by fashioning a garment from the textile or using a sheet or cover. The radiation-shielding textile found to be suitable is a cloth woven of yarn consisting of a textile fibre, such as nylon, and from two to thirty-five percent by weight of conductive metal filament.

5 Claims, 3 Drawing Figures

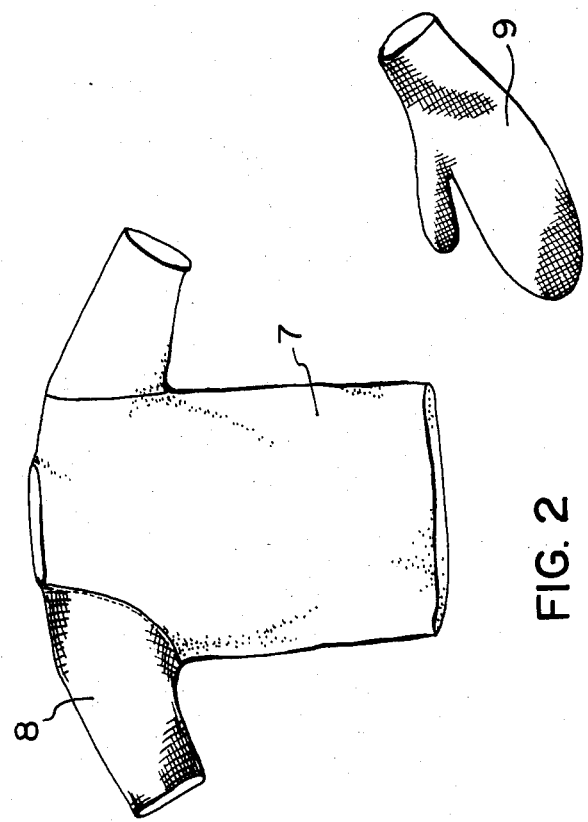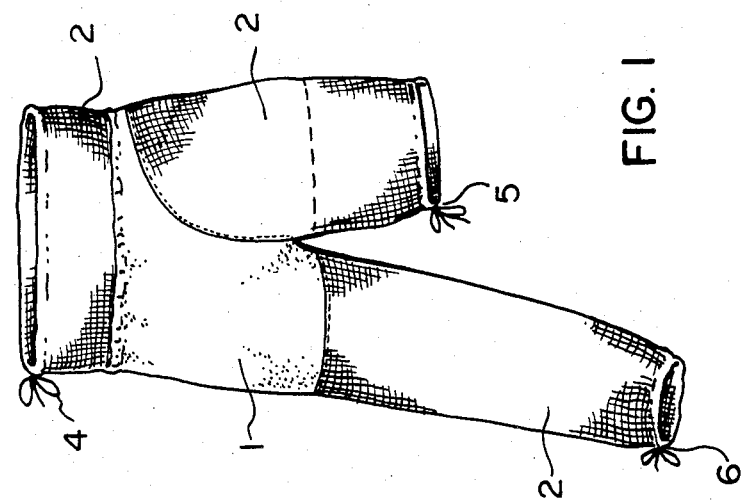

METHOD AND ARTICLE FOR PAIN REDUCTION USING RADIATION-SHIELDING TEXTILE

BACKGROUND OF THE INVENTION

1. Field of the Invention

The present invention relates to methods of pain treatment. In particular, it relates to a method for reducing phantom limb pains, stump pains and stump spasms in amputees, arthritic pains and other pains related to severed or damaged nerve endings.

2. Description of the Prior Art

The phenomenon of phantom limb sensation and phantom limb pain has been documented for several years, but the cause of the phenomenon has not been adequately explained. According to this phenomenon, an amputee will have a sensation of pain in a limb or extremity despite the fact that the actual limb or extremity has been amputated. Such pains may be persistent and severe and may disrupt the sufferer's sleep. Up to the present, the only effective treatment for such pains has been by the use of pain-killing drugs. Surgical treatment of the nerves in the stump, ultrasound and hot wax treatments, physiotherapy and injections of sclerosing or anesthetic agents have all been tried without success.

According to one theory, the nervous system is normally shielded by a healthy layer of skin from electromagnetic radiation or random electric currents, whether from the sun or other sources both natural and manmade. In the case of an amputee, part of the layer of skin is destroyed and is replaced by scar tissue, and nerve ends are thereby exposed to electromagnetic radiation or random electric currents. The nerve itself may have been severed, leaving it more susceptible to the effects of radiation. A possible effect of radiation impinging on the nerve end is to generate an electrical signal in the nerve which is interpreted by the brain as a pain signal from the amputated limb.

The concept of electromagnetic shielding is well known. A sheet of conductive material placed between points A and B serves to shield point A from changes in an electromagnetic field occuring at B. The same effect is approximated when a grid or network of conductors is substituted for the sheet of conductive material. Such a grid is sometimes referred to as a Faraday cage, particularly when an object is completely surrounded by such grid to shield it from changing electromagnetic fields. For example, a grounded Faraday cage may be used to shield an object from lightning.

Textile materials which are partly woven from metallic fibers are well known for various uses. One reason for including metallic fibers in textiles has been the esthetic appearance of the fabric. Textiles containing metal fibers have also been used to increase the strength and resistance to stretching of the fabric, to provide a heat reflecting fabric for use in protective clothing, or to form an electrically conductive fabric for use in clothing to reduce the build-up of static charges and avoid the dangers created by static discharges through sparking. Various methods are known for manufacturing such textiles. One known method is to weave the textile from a yarn composed of a relatively small quantity of metal filaments, whether continuous or discontinuous, along with the textile fiber.

SUMMARY OF THE INVENTION

The present invention provides a method of alleviating pain resulting from exposed or damaged nerve ends such as the phantom limb pain in amputees by shielding the scarred stump area from electromagnetic radiation. The method comprises the step of shielding the stump or arthritic area with a cloth woven from a yarn containing threads of a conductive metal. Such method has also been found to be effective to reduce stump spasms and stump pains in amputees, pain from scars other than those resulting from amputation and also arthritic pain and menstrual pain and cramps. The yarn is preferably composed of from 2 to 35% by weight of conductive metal filament, and the balance of natural or synthetic textile fiber such as nylon. The metal may be any conductor, but a stainless steel alloy has been found to be effective.

BRIEF DESCRIPTION OF THE DRAWINGS

In drawings which illustrate embodiments of the invention:

FIG. 1 illustrates leggings to be worn by a leg amputee according to the method of the invention;

FIG. 2 illustrates a shirt which may be used also according to the method of the present invention; and, FIG. 3 illustrates a mitt of a type used according to the method of the invention.

DETAILED DESCRIPTION OF AN EMBODIMENT OF THE INVENTION

At the basis of the present invention is the discovery that phantom limb pains, stump pains, stump spasms and scar pains in amputees may be reduced or eliminated by covering the stump or scarred area with an appropriate metallic cloth. Apparently the cloth acts much as a Faraday cage to shield the scarred area from changing electromagnetic fields or random electric currents which otherwise would stimulate unprotected nerve endings resulting in phantom limb pains.

According to the method of the invention, the scar tissue on the stump should be covered with one or more layers of the appropriate metallic cloth, so that the cloth overlaps the scarred area. Direct skin contact is not required. A suitable method of covering the affected area is to fashion a piece of clothing partly from the metallic cloth material so that the amputee may, by wearing the article of clothing, cover the stump area and any other scar tissue with the metallic cloth. For example, FIG. 1 shows pants or leggings 1 which have been successfully used by an amputee whose left leg had been amputated five inches below the groin. The shaded areas 2 constitute the appropriate metallic cloth. In this case, the amputee also had a shrapnel wound in the right knee, and an abdominal scar resulting from an appendectomy. A drawstring is provided at 5 to complete the coverage of the left stump. A drawstring was also provided at 6 to tighten the coverage of the material around the scarred area on the right knee. Similarly a drawstring at 4 was provided to complete the coverage of the abdominal scar area. FIG. 2 shows a short-sleeved shirt 7 which is partly sewn using the appropriate metallic cloth 8 in an area to reduce either phantom limb pain in the case of a person whose right arm has been amputated, or arthritic pain in the case of an arthritic afflicted in the right shoulder. Where one or more fingers have been amputated, or the person suffers from arthritis in the joints of the hand, a mitt 9 may be completely sewn from the appropriate metallic cloth as shown in FIG. 3.

The method of the present invention has also been found to alleviate menstrual pains and cramps. Such pains and cramping may occur periodically in females and may be quite debilitating. The patient's sleep may be disturbed. It has been found that wrapping the suitable metallic cloth around the lower body while sleeping considerably alleviates such pain and cramping and permits uninterrupted sleep.

For complete relief, the article of clothing is worn both day and night, or whenever the pain recurs. Where the main problem is pain-induced disruption of sleep, the article of clothing may only be worn at night. Alternatively, a bed sheet composed of the appropriate metallic cloth will also reduce the pain.

A suitable cloth for the practice of the method of the invention which both provides the appropriate electromagnetic shielding and the comfort of a standard non-metallic textile is a fabric sold under the trade mark FARABLOC. The yarn from which the textile is woven is composed of approximately 13% by weight of stainless steel filaments. The balance of the yarn is a synthetic nylon fiber such as nylon 66. The yarn has an electrical conductance of approximately 330 ohms per centimeter. The fabric has a warp of 24.5 threads per centimeter and a woof of 24.5 threads per centimeter. The weight of the fabric is approximately 200 grams per square meter. The binding is L 1/1—that is, one thread up and one thread down. Other conductive metals would be suitable, such as copper or silver. Other natural or synthetic fibers would also be suitable to comprise the yarn. It would also be suitable to utilize cloth woven of alternate threads of metal and textile fiber.

Case Study 1

The end of the index finger on the right hand of the patient had been sheared off in an industrial accident. A number of operations had removed the stump of the finger. The patient had suffered daily. Chills, throbbing and itching in the area of the amputated finger were experienced and occasional phantom pains which felt like a nail being driven through the amputated finger and the sensation that the finger was being stretched occurred. These sensations occurred mostly at night. Nothing had served to alleviate the phantom pains. On occasion, the whole hand would go into a spasm. Temporary relief of this latter affliction was provided by pain killers, ultrasound therapy and hot wax therapy.

A single mitt as shown in FIG. 3 was fashioned for the patient from the metallic cloth described above. The mitt was worn in the evenings and while driving to work. The patient found that quick and effective relief from the pain resulted from wearing the mitt and the patient was now able to sleep comfortably.

Case Study 2

The patient had been injured in World War II by shrapnel and gun shots resulting in fracture of the left leg and a groin aneurism. Eventually, the left leg was amputated five inches below the groin. Some shrapnel still remained in the right knee. The patient also suffered from arthritis in the right shoulder. The patient suffered from constant phantom limb sensation in the left limb, and periodic excruciating phantom limb pain. Nothing was found to alleviate the phantom limb sensation, although immersion in hot water, massage and pain killing drugs would provide temporary relief from the phantom limb pain. Stump spasms or "stump jump" would also occur periodically. The patient's pajama bottoms were altered by sewing the metallic cloth into the pants as shown in FIG. 1. A portion of the fabric was also sewn into the right shoulder of a t-shirt as shown in FIG. 2. The patient wore the garment over a number of months and during this period suffered no symptoms of phantom limb pains. In addition, the pain in his arthritic shoulder was alleviated. The patient was able to discontinue the use of prescription pain-killing drugs.

Case Study 3

The patient's left leg had been amputated eight inches below the groin as a result of cancer in the calf muscle and knee. The patient suffered daily phantom limb sensation and periodic intense phantom limb pain in the left leg. Massaging the stump would alleviate the phantom limb sensation. Nothing was found to alleviate the phantom limb pain. The patient also suffered from painful "stump jump" periodically, and again nothing was found to relieve the pain. A garment was fashioned having the metallic cloth covering the stump of the patient and the garment was worn when attacks of the pain occurred. The patient found that within $\frac{3}{4}$ of an hour to one hour of covering the stump with the cloth, the phantom limb pain completely disappeared. During a test period of ten weeks, the garment worked successfully on at least five occasions.

Case Study 4

The patient's left arm was crushed in an industrial accident and the patient was left with heavy scarring and only partial use of the arm. Arthritis developed and the patient suffered severe pain in the arm. His sleep was constantly disturbed. A long sleve of the metallic cloth was sewn onto a t-shirt which the patient wore at night. The patient found that the amount of pain suffered was reduced by at least two-thirds. The disturbance of sleep was reduced and the need for pain killing drugs was almost eliminated.

Case Study 5

The patient was born with a foot deformity which resulted in damage to the knees. Surgery was performed but arthritis eventually developed in the knees. The patient suffered recurring pain in the knees which seriously affected sleep. A piece of the metallic textile was used to cover the knees, and the patient found that the pain was decreased considerably. The disturbance of sleep was eliminated and the amount of pain killing drugs which were required was reduced.

Of the sufferers of chronic pain who have been tested by the method of the present invention to date, in 12.5% of the cases, the treatment had no noticeable effect. 62.5% of the cases showed successful results from the use of the metallic textile in that the need for analgesics was substantially eliminated. The method has been found to successfully reduce pain in 60 to 70% of cases studied.

While a woven cloth has been specified in the description of the preferred embodiment, it will be apparent to those skilled in the art that a non-woven cloth having a grid of conductive metallic filaments will also operate effectively in the method of the invention while retaining the qualities of a non-metallic fabric. As will also be apparent to those skilled in the art in light of the foreging disclosure, many variations in the type of metallic thread or yarn and textile fibers used in the cloth and in the manner of weaving the cloth are possible in the practice of this invention without departing from the scope thereof. Accordingly, the scope of the invention is to be construed in accordance with the substance defined by the following claims.

I claim:

1. A method of alleviating pain and discomfort in humans comprising the step of shielding painful or scarred areas with a cloth comprising between two and thirty-five percent by weight of a continuous system of electrically conductive stainless steel fibres over a period of time sufficient to reduce said pain and discomfort.

2. The method of claim 1 wherein said pain and discomfort comprises phantom limb pains and said shielded areas comprise a stump of an amputated appendage.

3. The method of claim 1 wherein said pain and discomfort comprises arthritic pain.

4. The method of alleviating pain and discomfort in humans comprising the steps of:

(i) constructing an article of clothing suitable to be worn over painful or scarred areas, said article of clothing comprising in a region large enough to completely cover said painful or scarred areas, a metallic cloth comprising between two and thirty-five percent by weight of a continuous system of electrically conductive stainless steel fibres; and (ii) said human wearing said article of clothing in a manner whereby said painful or scarred areas are completely covered by said metallic cloth over a period of time sufficient to reduce said pain and discomfort.

5. An article of human wearing apparel adapted to be worn for the purpose of alleviating pain and discomfort by the method of claim 2, said article of wearing apparel being configured to conform to a stump and comprising in the region adapted to be positioned over said stump a metallic cloth comprising between two and thirty-five percent by weight of electrically conductive stainless steel fibres.

* * * * *